US012329442B2

(12) United States Patent
Smith et al.

(10) Patent No.: US 12,329,442 B2
(45) Date of Patent: Jun. 17, 2025

(54) MULTIFUNCTIONAL ELECTROSURGICAL INSTRUMENTS WITH DYNAMIC ELECTRODE ASSEMBLIES

(71) Applicant: Boston Scientific Scimed, Inc., Maple Grove, MN (US)

(72) Inventors: Paul Smith, Smithfield, RI (US); Jose Garcia-Cordero, Ocala, FL (US); Kevin James McElwee, Franklin, MA (US); Ramon Estevez, Lowell, MA (US); Allyn Narcisse Jensrud, Brookline, MA (US); Irina Pyataeva, Moscow (RU); Samuel Raybin, San Jose, CA (US); Mingxiang Xu, Wayland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 320 days.

(21) Appl. No.: 16/393,263

(22) Filed: Apr. 24, 2019

(65) Prior Publication Data
US 2019/0328451 A1    Oct. 31, 2019

Related U.S. Application Data

(60) Provisional application No. 62/662,601, filed on Apr. 25, 2018.

(51) Int. Cl.
*A61B 18/14* (2006.01)
*A61B 18/00* (2006.01)

(52) U.S. Cl.
CPC ............. *A61B 18/1477* (2013.01); *A61B 2018/00601* (2013.01); *A61B 2018/1427* (2013.01); *A61B 2018/1475* (2013.01)

(58) Field of Classification Search
CPC ...... A61B 18/1477; A61B 2018/00601; A61B 2018/1427; A61B 2018/1475;
(Continued)

(56) References Cited

U.S. PATENT DOCUMENTS 4,222,380 A * 9/1980 Terayama ......... A61M 25/0084
604/164.01
5,454,809 A * 10/1995 Janssen ............. A61B 18/1206
606/41
(Continued)

FOREIGN PATENT DOCUMENTS

EP       3 381 391 A1    10/2018
KR    2016-0141684 A    12/2016
(Continued)

OTHER PUBLICATIONS

Rui Huang et al., "Comparison of O-Type HybridKnife to Conventional Knife in Endoscopic Submucosal Dissection for Gastric Mucosal Lesions," Medicine, Apr. 2016, pp. 1-6, vol. 95, No. 13, Wolters Kluwer Health, Inc,, www.md-journal.com.
(Continued)

*Primary Examiner* — Linda C Dvorak
*Assistant Examiner* — Lindsay Regan Lancaster
(74) *Attorney, Agent, or Firm* — Bookoff McAndrews, PLLC

(57) ABSTRACT

According to one aspect, an instrument may include a sheath having a distal end. The instrument also may include a fluid cannula at the distal end of the sheath. The instrument also may include a cutting electrode at the distal end of the sheath. At least one of: (i) an exterior surface of the fluid cannula, and (ii) a cutting electrode surface that faces the exterior surface, is longitudinally slidable along the other of the exterior surface and the cutting electrode surface during movement of at least one of the cutting electrode and the
(Continued)

fluid cannula relative to the other of the cutting electrode and the fluid cannula.

20 Claims, 7 Drawing Sheets

(58) Field of Classification Search
CPC .... A61B 2018/00982; A61B 2218/002; A61B 2018/00196; A61B 2018/00577; A61B 2018/00946; A61B 2018/00958; A61B 2018/1425; A61M 5/162
See application file for complete search history.

(56) References Cited

U.S. PATENT DOCUMENTS

| | | | | |
|---|---|---|---|---|
| 5,662,680 | A * | 9/1997 | Desai | A61B 18/1477 606/210 |
| 5,944,715 | A * | 8/1999 | Goble | A61B 18/1485 606/41 |
| 5,944,716 | A * | 8/1999 | Hektner | A61B 18/1492 606/41 |
| 5,961,526 | A * | 10/1999 | Chu | A61B 17/32056 606/113 |
| 5,995,875 | A * | 11/1999 | Blewett | A61B 18/1477 606/41 |
| 6,007,546 | A * | 12/1999 | Snow | A61B 18/14 606/113 |
| 6,086,565 | A * | 7/2000 | Ouchi | A61B 17/34 604/93.01 |
| 6,123,665 | A * | 9/2000 | Kawano | A61B 17/3478 606/113 |
| 6,669,691 | B1 * | 12/2003 | Taimisto | A61B 18/1482 606/41 |
| 7,063,696 | B2 * | 6/2006 | Taimisto | A61B 18/1482 128/898 |
| 10,470,816 | B2 | 11/2019 | Zhou et al. | |
| 2004/0087935 | A1 * | 5/2004 | Taimisto | A61B 18/1492 606/41 |
| 2004/0210284 | A1 * | 10/2004 | Okada | A61B 18/1402 607/96 |
| 2005/0020965 | A1 * | 1/2005 | Rioux | A61M 25/007 606/41 |
| 2005/0273092 | A1 * | 12/2005 | G. | A61B 18/1477 606/41 |
| 2008/0125775 | A1 * | 5/2008 | Morris | A61B 18/1477 606/50 |
| 2011/0028962 | A1 * | 2/2011 | Werneth | A61B 18/1492 606/41 |
| 2013/0261621 | A1 | 10/2013 | Kramer et al. | |
| 2014/0288554 | A1 * | 9/2014 | Okada | A61B 18/1492 606/45 |
| 2016/0008063 | A1 * | 1/2016 | Wake | A61B 17/3203 606/49 |
| 2016/0143662 | A1 * | 5/2016 | Mulier | A61B 18/1492 606/49 |
| 2016/0220301 | A1 * | 8/2016 | Yamamoto | A61B 18/14 |
| 2016/0235469 | A1 * | 8/2016 | Prisco | A61B 18/1485 |
| 2017/0224411 | A1 * | 8/2017 | Onuki | A61B 18/1492 |
| 2018/0263681 | A1 * | 9/2018 | Shuman | A61B 18/1492 |
| 2018/0368909 | A1 * | 12/2018 | Zhou | A61B 1/00087 |
| 2020/0390494 | A1 * | 12/2020 | Jeon | A61B 18/1482 |

FOREIGN PATENT DOCUMENTS

| | | |
|---|---|---|
| WO | WO 97/36548 A1 | 10/1997 |
| WO | WO-2016018457 A1 * | 2/2016 ......... A61B 18/1492 |

OTHER PUBLICATIONS

International Search Report and Written Opinion of the International Search Authority dated Oct. 27, 2020, issued in corresponding International Application No. PCT/US2019/028874, filed Apr. 24, 2019 (7 pages).

* cited by examiner

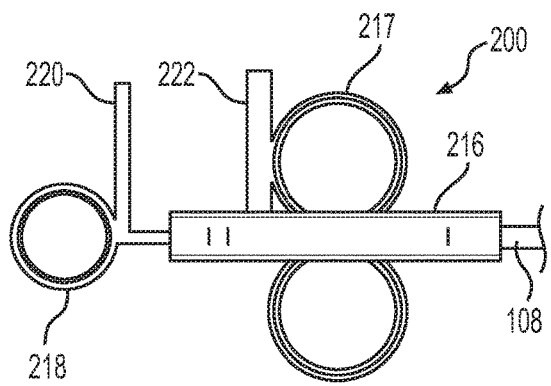
FIG. 2(A)(I)
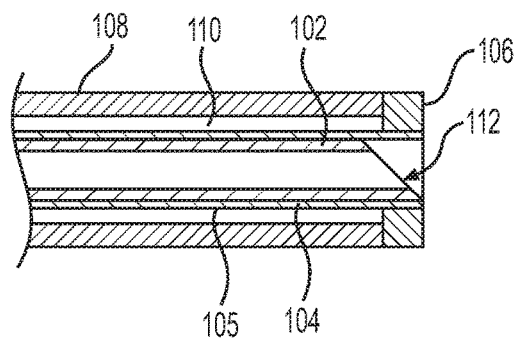
FIG. 2(A)(II)
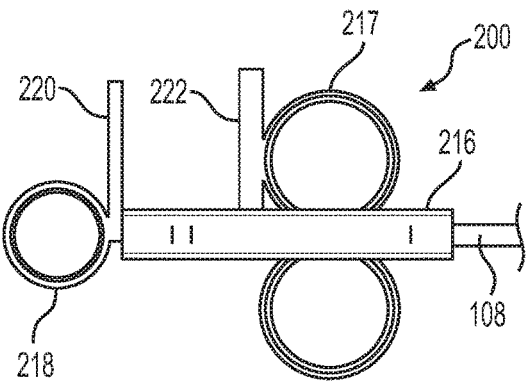
FIG. 2(B)(I)
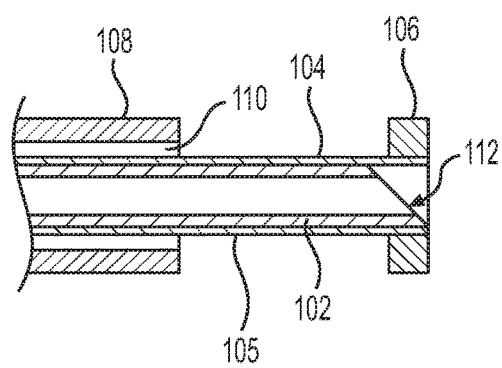
FIG. 2(B)(II)
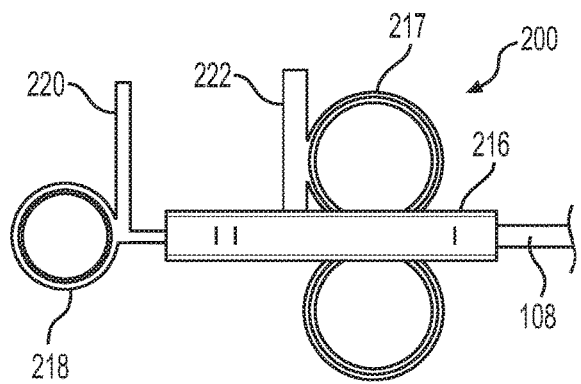
FIG. 2(C)(I)
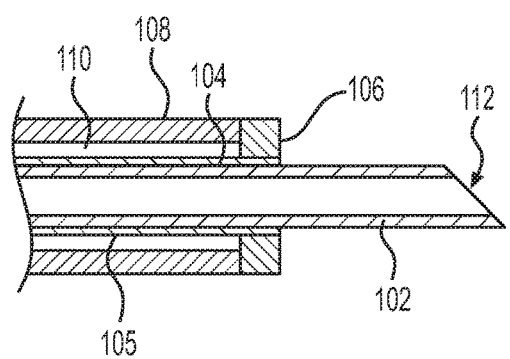
FIG. 2(C)(II)

MULTIFUNCTIONAL ELECTROSURGICAL INSTRUMENTS WITH DYNAMIC ELECTRODE ASSEMBLIES

CROSS-REFERENCE TO RELATED APPLICATIONS

This application claims the benefit of priority from U.S. Provisional Application No. 62/662,601, filed on Apr. 25, 2018, which is incorporated by reference herein in its entirety.

TECHNICAL FIELD

The present disclosure relates generally to surgical instruments and related methods. More particularly, the present disclosure relates to multifunctional electrosurgical instruments with dynamic electrode assemblies.

BACKGROUND

Electrosurgery may involve the application of various types of high-frequency electrical energy to biological tissue to, for example, cut, coagulate, dissect, resect, ablate, perforate, or fulgurate tissue. In some electrosurgical procedures, a physician may use an injection needle to inject fluid into tissue, to create separation between an overlying layer of tissue and an underlying layer of tissue, before cutting the overlying tissue with a separate electrosurgical instrument. Conventionally, this involves switching between using the injection needle and the electrosurgical instrument, which can add time and complexity to procedures. There is a need for a multifunctional electrosurgical instrument that may inject fluid into tissue, and cut tissue, to help reduce the overall length and complexity of a procedure.

SUMMARY

Embodiments of the present disclosure relate to, among other things, multifunctional electrosurgical instruments with dynamic electrode assemblies. Each of the embodiments disclosed herein may include one or more of the features described in connection with any of the other disclosed embodiments.

According to aspects of the present disclosure, an instrument may include a sheath having a distal end. The instrument also may include a fluid cannula at the distal end of the sheath. The instrument also may include a cutting electrode at the distal end of the sheath. At least one of: (i) an exterior surface of the fluid cannula, and (ii) a cutting electrode surface that faces the exterior surface, is longitudinally slidable along the other of the exterior surface and the cutting electrode surface during movement of at least one of the cutting electrode and the fluid cannula relative to the other of the cutting electrode and the fluid cannula.

The instrument may also include one or more of the features below. At least one of the cutting electrode and the fluid cannula may be movable relative to the sheath between an extended configuration relative to the distal end of the sheath and a retracted configuration relative to the distal end of the sheath. The cutting electrode and the fluid cannula may be movable relative to the sheath between respective extended configurations relative to the distal end of the sheath and respective retracted configurations relative to the distal end of the sheath. The cutting electrode surface may be an interior surface of the cutting electrode. The cutting electrode surface may be a radially-inner surface of the cutting electrode. The cutting electrode surface may be one of a plurality of spaced-apart cutting electrode surfaces that face the exterior surface of the fluid cannula. The cutting electrode may include a tubular portion, and the cutting electrode surface may be an interior surface of the tubular portion. The cutting electrode may include an enlarged distal portion at a distal end of the tubular portion, and the enlarged distal portion may be wider than the tubular portion. The fluid cannula may terminate at a distal point configured to pierce the tissue. At least one of the cutting electrode and the fluid cannula may be movable relative to the other of the cutting electrode and the fluid cannula to position a distal end of the fluid cannula distal to a distal end of the cutting electrode. At least one of the cutting electrode and the fluid cannula may be movable relative to the other of the cutting electrode and the fluid cannula to position a distalmost end of the fluid cannula within a distal end of the cutting electrode. The fluid cannula and the cutting electrode may be movable from a first configuration, in which the fluid cannula and the cutting electrode may be independently movable, to a second configuration, in which the fluid cannula and the cutting electrode may be coupled so as to move in unison. At least a portion of the fluid cannula may be electrically conductive.

According to other aspects of the present disclosure, an instrument may include a sheath having a distal end. The instrument also may include a first electrode at the distal end of the sheath. The first electrode may include a passage extending therethrough for directing a fluid through the first electrode. The first electrode also may include a distal opening from which the fluid is emitted from the first electrode. The instrument may further include a second electrode at the distal end of the sheath. An exterior surface of the second electrode may be configured to cut tissue. Also, at least one of the first and second electrodes may be movable relative to the other of the first and second electrodes. At least a portion of the second electrode may slidably receive at least a portion of the first electrode. The instrument may further include one or more of the features below. A handle assembly may be at a proximal end of the sheath. The handle assembly may include a first actuator, and movement of the first actuator may move the first electrode relative to at least one of the distal end of the sheath and the second electrode. The handle assembly may further include a second actuator, and movement of the second actuator may move the second electrode relative to at least one of the distal end of the sheath and the first electrode. The handle assembly may further include a handle body, and the first and second actuators may each slidably couple to the handle body, and the sheath may be fixed relative to the handle body. At least one of the first and second actuators may be rotatably coupled to the handle body, such that rotation of the at least one of the first and second actuators relative to the handle body rotates at least one of the first and second electrodes about at least one of their respective central longitudinal axes. The central longitudinal axes of the first and second electrodes may be coaxial.

According to others aspects of the present disclosure, an instrument may include a sheath having a distal end. The instrument also may include an inner member at the distal end of the sheath. The inner member may include a passage extending therethrough for directing a fluid through the inner member. The inner member also may include a distal opening from which the fluid is emitted from the inner member. The instrument may further include a outer member at the distal end of the sheath. An exterior surface of the outer member may be configured to cut tissue. Also, at least one of the inner and outer members may be movable relative to the other of the inner and outer members. At least a portion of the outer member may slidably receive at least a portion of the inner member. At least one of the inner member and the outer member may be an electrode.

According to further aspects of the present disclosure, a method for treating tissue in a target area of a subject may include positioning a distal end of an instrument at the target area. The method may also include moving at least one of a first electrode and a second electrode, at the distal end of the instrument, relative to the other of the first and second electrodes, to position a distal end of the first electrode distal to a distalmost end of the second electrode. The method may also include puncturing the tissue with the distal end of the first electrode. The method may further include injecting fluid into the tissue through the first electrode to raise the tissue. The method may also include moving at least one of the first and second electrodes relative to the other of the first and second electrodes, to cover at least a portion of the first electrode with a distal end of the second electrode. Also, the method may include energizing the second electrode with electrical energy to cut the raised tissue. The foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal."

BRIEF DESCRIPTION OF THE DRAWINGS

The accompanying drawings are incorporated in and constitute a part of this specification. These drawings illustrate aspects of the present disclosure that, together with the written descriptions herein, serve to explain this disclosure as follows:

FIG. 1A illustrates a cross-sectional view of a distal portion of the exemplary instrument, and FIG. 1B illustrates a side view of a proximal portion of the exemplary instrument.

FIGS. 2(A)(I) and 2(A)(II) illustrate a side view of the proximal portion and a close-up cross-sectional view of the distal portion, respectively, of the exemplary instrument of FIGS. 1A and 1B, in a first state.

FIGS. 2(B)(I) and 2(B)(II) illustrate another side view of the proximal portion and another close-up cross-sectional view of the distal portion, respectively, of the exemplary instrument of FIGS. 1A and 1B, in a second state.

FIGS. 2(C)(I) and 2(C)(II) illustrate another side view of the proximal portion and another close-up cross-sectional view of the distal portion, respectively, of the exemplary instrument of FIGS. 1A and 1B, in a third state.

DETAILED DESCRIPTION

Reference will now be made in detail to embodiments of the present disclosure, examples of which are illustrated in the accompanying drawings. Wherever possible, the same reference numbers will be used throughout the drawings to refer to the same or like parts. The term "distal" refers to the end farthest away from a user when introducing a device into a subject. The term "proximal" refers to the end closest to the user when placing the device into the subject. For example, a proximal direction and a distal direction are identified using arrows in FIG. 1A. When used herein, the terms "approximately" and "substantially" may indicate a range of values within +1-5% of a stated value.

Figure 1A:
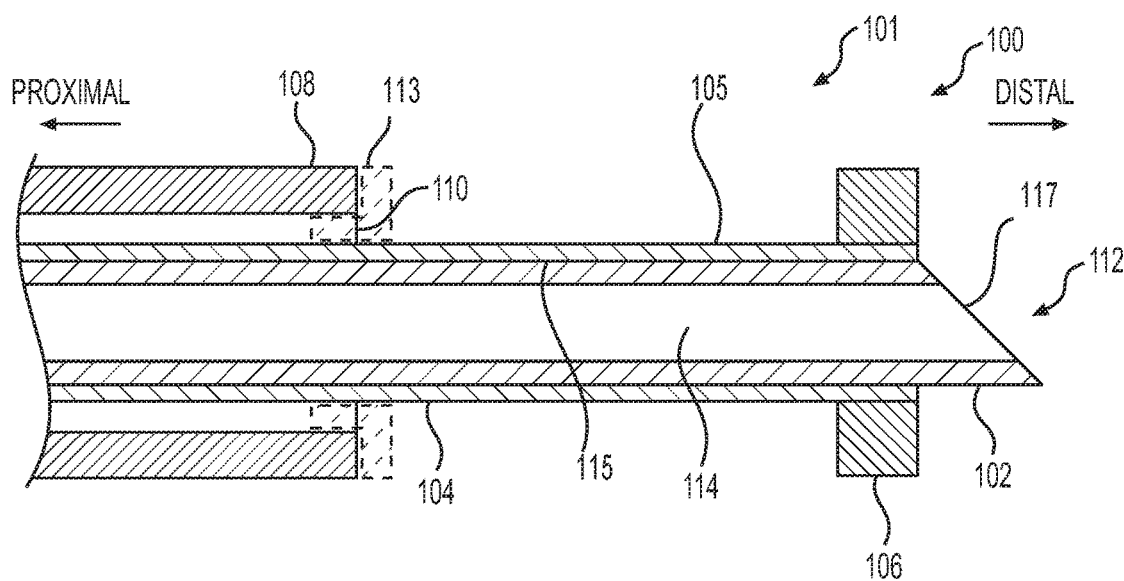
FIGS. 1A and 1B illustrate views of portions of an exemplary instrument, according to aspects of the present disclosure. More particularly.
Figure 1B:
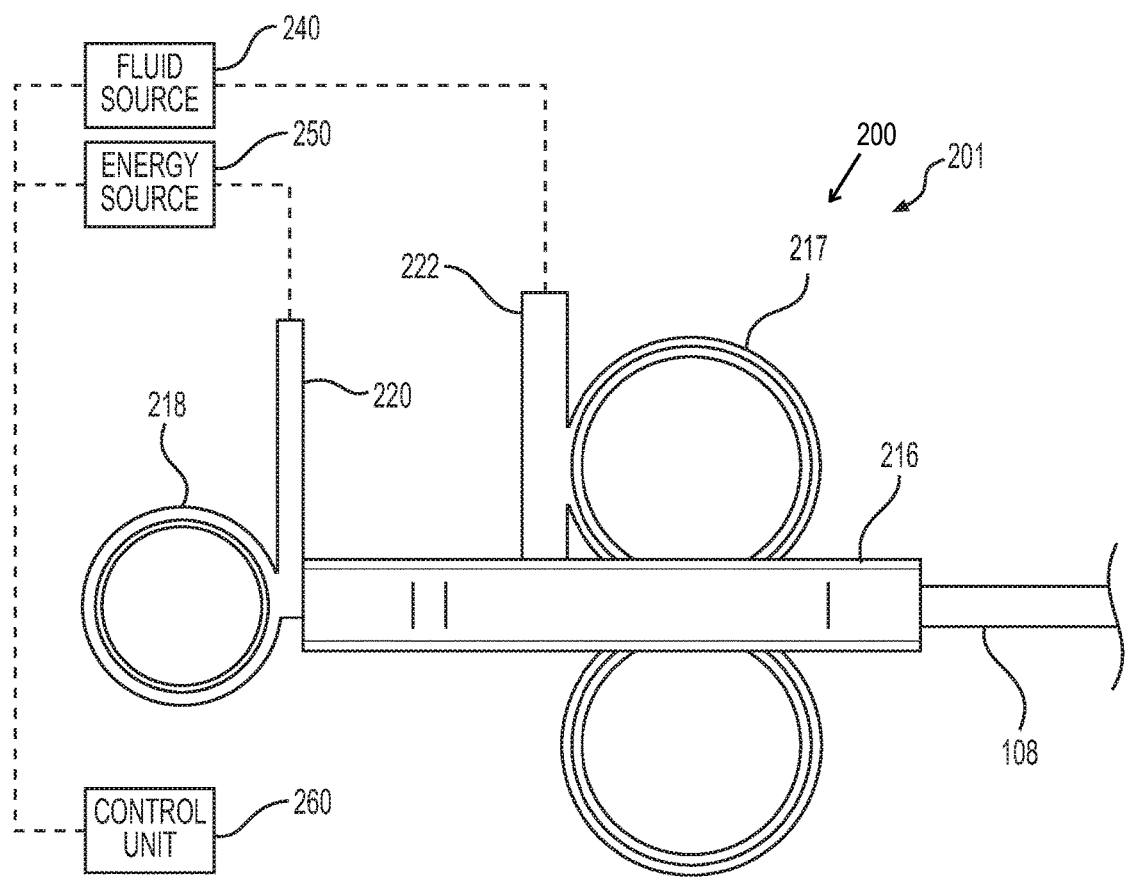

FIGS. 1A and 1B illustrate portions of an exemplary instrument 100. Instrument 100 may include a proximal portion 201 (FIG. 1B) and a distal portion 101 (FIG. 1A). A sheath 108 may extend from the proximal portion 201 to the distal portion 101. Distal portion 101 may include a distal end of sheath 108, an inner member 102, and an outer member 104. Inner member 102 and outer member 104 may be configured to be extended, in the distal direction, from the distal end of sheath 108; and also to be retracted, in the proximal direction, into the distal end of sheath 108. Distal portion 101 of instrument 100 may be cylindrical and may have curved longitudinal sides to facilitate insertion into a body of a patient. In some examples, distal portion 101 may have a rectangular, pentagonal, hexagonal, heptagonal, octagonal, or any other suitable cross-sectional shape. Distal portion 101 may be flexible to facilitate navigation through a subject's anatomy, which may include one or more apertures, cavities, and tortuous passages. The same characteristics may be present in sheath 108, inner member 102, and/or outer member 104, which are part of distal portion 101.

Inner member 102 may be received within outer member 104, and outer member 104 may be received within sheath 108. Inner member 102, outer member 104, and sheath 108 may be concentrically arranged, and one or more of inner member 102, outer member 104, and sheath 108 may extend from distal portion 101 to proximal portion 201. A radially-outer surface of inner member 102 may be adjacent to or in contact with a radially-inner surface of outer member 104. A radially-outer surface of outer member 104 may be adjacent to, in contact with, or spaced apart from a radially-inner surface of sheath 108. In one example, an air gap 110 may separate outer member 104 from sheath 108. To prevent material from entering air gap 110, a ceramic tip 113 may be inserted into the distal end of sheath 108 to plug the distal end of air gap 110. Ceramic tip 113 may include a central lumen for receiving inner and outer members 102 and 104.

A lumen 114 may extend through inner member 102, and may terminate at an opening 117 at the distal end of inner member 102. In some examples, lumen 114 may be centered along a central longitudinal axis of distal portion 101, inner member 102, outer member 104, and/or sheath 108. Inner member 102 may include a distal end 112 configured to pierce tissue. In one example, distal end 112 may be pointed (e.g., having a sharpened or tapered tip, including one with a single bevel, one that is multi-beveled, one that is conical-tapered, franseen, touhy, backcut, withacre, and/or trocared). Alternatively, distal end 112 may be blunt (e.g., having a flat or rounded tip). The blunt tip version of distal end 112 may pierce tissue with assistance from, for example, electrical energy applied via distal end 112.

Lumen 114 may be configured to deliver fluid to distal end 112, where the fluid may be emitted into tissue via opening 117. Inner member 102 may be connected to a fluid source 240 (FIG. 1B) for supplying fluid into lumen 114. In some examples, inner member 102 may be conductive, and may receive electrical energy, allowing the electrical energy to flow from inner member 102 to tissue. For example, electrical energy may flow from energy source 250 to outer member 104, which also may be conductive, and from outer member 104 to inner member 102. Additionally or alternatively, inner member 102 may receive electrical energy directly from energy source 250 via any other suitable conductive pathway, including one or more wires (not shown) extending between energy source 250 and inner member 102. In such an example, outer member 104 may be non-conductive. In another example, inner member 102 may be non-conductive, while outer member 104 may be conductive and may receive electrical energy from energy source 250. This description of conductivity/non-conductivity may also apply to other pairs of inner and outer members described herein. Inner member 102 may be extendable and retractable relative to the distal end of sheath 108. Additionally or alternatively, inner member 102 may be may be movable proximally and distally relative to outer member 104.

Outer member 104 may include a shaft 105 and a protrusion 106 coupled to the distal end of shaft 105. Protrusion 106 may protrude radially-outwardly from the distal end of shaft 105. Protrusion 106 may include a circular disc surrounding shaft 105. In some examples, protrusion 106 may be positioned at the distalmost end of shaft 105. In other examples, protrusion 106 may be positioned proximate to the distalmost end of shaft 105, or at any other position on shaft 105 depending on factors including, for example, the type of procedure being performed.

Shaft 105 may include a recess, cavity, opening, and/or lumen 115 that receives inner member 102. Lumen 115 may extend longitudinally from distal portion 101 to proximal portion 201. In some examples, outer member 104 may receive electrical energy from energy source 250 (FIG. 1B), either directly or through inner member 102 as an intermediary, and may emit electrical energy from shaft 105 and/or protrusion 106. Both shaft 105 and protrusion 106 may be conductive. Alternatively, one of shaft 105 and protrusion 106 may be conductive, while the other of shaft 105 and protrusion 106 may be non-conductive. Or, shaft 105 and protrusion 106 may be non-conductive, and inner member 102 may be conductive and used to cut or otherwise affect tissue. Outer member 104 may be extendable and retractable from the distal end of sheath 108, and/or movable proximally and distally relative to inner member 102.

In some examples, the central longitudinal axis of outer member 104 may be coaxial with at least one of a central longitudinal axis of inner member 102 and/or sheath 108. A radially-inner surface of shaft 105 may be slidably engaged with a radially-outer surface of inner member 102 such that opposing, contacting surfaces of inner member 102 and shaft 105 may slide relative to each other.

Inner member 102 and outer member 104 also may slide, or otherwise move via longitudinal translation, relative to the distal end of sheath 108. In some examples, each of inner member 102, outer member 104, and sheath 108 may move independently from the others. In other examples, two of inner member 102, outer member 104, and sheath 108 may be coupled to each other and may move in unison.

FIG. 1B illustrates a proximal portion 201 of instrument 100. Proximal portion 201 may include a handle assembly 200. Handle assembly 200 may include a handle body 216. Handle body 216 may be fixedly coupled to a proximal end of sheath 108. Handle body 216 may be configured to be held by a user of instrument 100. One or more actuators may be coupled to handle body 216. For example, an inner member actuator 217 may be coupled to handle body 216. Inner member actuator 217 may be coupled to inner member 102, such that movement of inner member actuator 217 may move inner member 102. An outer member actuator 218 also may be coupled to handle body 216. Outer member actuator 218 may be coupled to outer member 104, such that movement of outer member actuator 218 may move outer member 104. Handle assembly 200 may be coupled to fluid source 240 through a fluid connector 222, such that fluid from fluid source 240 may be directed into and through handle assembly 200, and may eventually flow to distal portion 101 and out of instrument 100. Handle assembly 200 also may be coupled to energy source 250 through an electrical connector 220, such that electrical energy may be directed into and through handle assembly 200, and may eventually be conducted to distal portion 101 and into target tissue. In some examples, an electronic control unit 260 may be used to control energy source 250 and/or fluid source 240.

Inner member actuator 217 may be distal to outer member actuator 218, and may slide longitudinally along handle body 216, in proximal and distal directions, to slide inner member 102 longitudinally, in proximal and distal directions, relative to sheath 108. Inner member actuator 217 may include opposed annular rings protruding from handle body 216, for receiving a user's fingers. In some examples, fluid connector 222 may be coupled to a portion of the annular rings. Fluid connector 222 may be in fluid communication with lumen 114 of inner member 102. A drive member 531 (FIG. 5) may transmit movement of inner member actuator 217 to inner member 102. Drive member 531 may include a portion of inner member 102 that extends proximally from distal portion 101 to inner member actuator 217.

Outer member actuator 218 may be coupled to outer member 104, such that movement of outer member actuator 218 results in corresponding movement of outer member 104. Outer member actuator 218 may be positioned at a proximal end of handle body 216 (FIG. 1B). In some examples, outer member actuator 218 may include an annular ring configured to receive a user's thumb. Electrical connector 220 may be coupled to outer member actuator 218. Electrical energy from energy source 250 may enter instrument 100 via electrical connector 220. Electrical connector 220 may include one or more wires, cables, or other conductors, which also may extend to outer member 104, for conducting the electrical energy to outer member 104 at distal portion 101. In some examples, electrical connector 220 may be electrically connected to both outer member 104 and inner member 102.

Outer member actuator 218 may slide longitudinally, in proximal and distal directions, relative to handle body 216, to move outer member 104, in proximal and distal directions, at distal portion 101. The user may slide outer member actuator 218 by moving his or her thumb. When an operator actuates outer member actuator 218, the outer member 104 may move longitudinally along a longitudinal axis of the outer member 104. A drive member 533 (FIG. 5) may transmit movement of outer member actuator 218 to outer member 104. Drive member 533 may include a portion of outer member 104 that extends proximally from distal portion 101 to outer member actuator 218. Inner member actuator 217 and outer member actuator 218 may move independently relative to each other. In other examples, two of inner member 102, outer member 104, and sheath 108 may be coupled at distal portion 101, resulting in the ability to move two of outer member actuator 218, inner member actuator 217, and sheath 108 in unison. Any of the exemplary instruments described herein may have any of the handle assemblies discussed herein.

FIGS. 2(A)(I), 2(A)(II), 2B(I), 2B(II), 2C(I), and 2(C)(II) illustrate distal and proximal portions 101 and 201 of instrument 100 in various states of operation. FIGS. 2(A)(I) and 2(A)(II) show an example of a first state of instrument 100, with inner member 102 completely housed within outer member 104, shaft 105 completely housed within sheath 108, and a proximal-facing surface of protrusion 106 contacting a distal-facing surface of sheath 108. Both inner member actuator 217 and outer member actuator 218 may be at their proximalmost positions relative to handle body 216, to put instrument 100 in this state. In another example, the distal end of inner member 102 may protrude distally from outer member 104 in the first state. Instrument 100 may be placed in the first state by sliding sheath 108 distally relative to inner and outer members 102 and 104, and/or by sliding inner and outer members 102 and 104 proximally relative to sheath 108. The first state may be configured for allowing delivery of distal portion 101 of instrument 100 to a target area of a subject's body without the risk of accidentally damaging other areas of the subject's body with inner member 102. Additionally or alternatively, the first state may be configured to allow use of protrusion 306 for marking tissue on which a procedure is to be performed.

FIGS. 2(B)(I) and 2(B)(II) show an example of a second state of instrument 100, with inner member 102 and outer member 104 protruding distally from the distal end of sheath 108, with inner member 102 completely housed within outer member 104. Both inner member actuator 217 and outer member actuator 218 may be at their distalmost positions relative to handle body 216, to put instrument 100 in the second state. When instrument 100 is in the second state, the first state (FIGS. 2(A)(I) and 2(A)(II)), and/or any state in between, protrusion 106 may be used to mark tissue to identify an area of the tissue on which a procedure may be performed. When instrument 100 is in the second state, shaft 105 and/or protrusion 106 may be used to cut tissue. Instrument 100 may be placed in the second state by sliding sheath 108 proximally relative to inner and outer members 102 and 104, and/or by sliding inner and outer members 102 and 104 distally relative to sheath 108.

FIGS. 2(C)(I) and 2(C)(II) show an example of a third state of instrument 100, wherein inner member 102 protrudes distally from outer member 104 and sheath 108. In this state, the user may pierce tissue with inner member 102, and insert inner member 102 into the tissue to a desired insertion depth. Once there, fluid can be injected into the tissue via inner member 102. The tissue may be pierced by the sharp tip at the end of inner member 102, or alternatively, by the blunt end (not shown) of inner member 102 with the assistance of electrical energy that energizes inner member 102. It is contemplated that the fluid may be injected with inner member 102 at any state of extension relative to outer member 104. It also is contemplated that outer member 104 may be placed in a partially extended state, relative to sheath 108, such that the distal-facing surface of protrusion 106 may act as a stop for abutting tissue to limit insertion of inner member 102 into the tissue to a predetermined depth. Instrument 100 may be placed in the third state by sliding sheath 108 and outer member 104 proximally relative to inner member 102, and/or by sliding inner member 102 distally relative to sheath 108 and outer member 104.

Figure 3A:
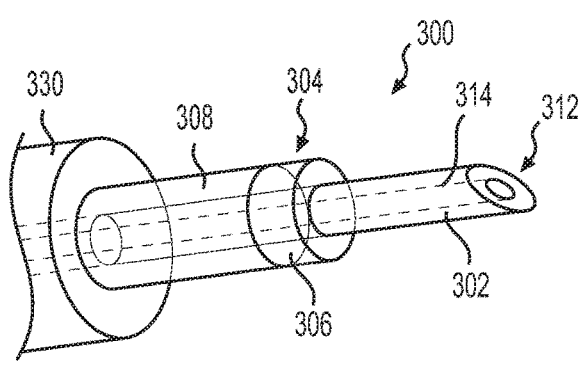
FIGS. 3A-3C illustrate perspective views of a distal portion of and exemplary instrument in various states, according to aspects of the present disclosure.
Figure 3B:
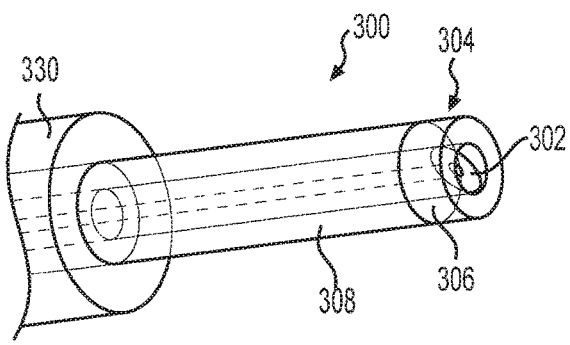
Figure 3C:
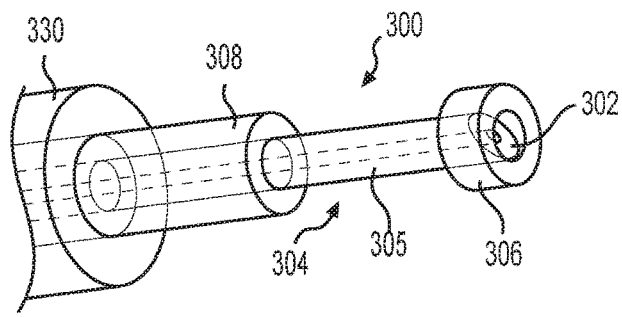

FIGS. 3A-3C illustrate another exemplary instrument 300, which may include a sheath 308, an inner member 302, and an outer member 304 (with a shaft 305 and a protrusion 306), similar to other instrument described herein. Instrument 300 is shown protruding distally from an outer sheath or introducer 330. Introducer 330 may include, for example, an endoscope. In a first state shown in FIG. 3A, inner member 302 is shown protruding distally from outer member 304. Shaft 305 is received within sheath 308. This may be a state of instrument 300 that is configured for fluid injection into tissue. In a second state shown in FIG. 3B, inner member 302 is shown housed within outer member 304, and shaft 305 housed within sheath 308. This may be a state of instrument 300 that is configured for marking tissue, and/or for delivering instrument 300 to a target area. Moving from the state of FIG. 3A to that of FIG. 3B may involve moving sheath 108 and outer member 304 distally relative to inner member 302, by moving inner member 302 proximally relative to sheath 308 and outer member 304, or by some combination of the two movements. In a third state shown in FIG. 3C, inner member is shown housed within outer member 304, and shaft 305 protruding distally from sheath 308. This may be a state of instrument 300 that is configured for cutting tissue. Moving from the state of FIG. 3B to that of FIG. 3C may involve moving sheath 308 proximally relative to inner member 302 and outer member 304, by moving inner member 302 and outer member 304 distally relative to sheath 308, and/or by some combination of these movements.

Figure 4A:
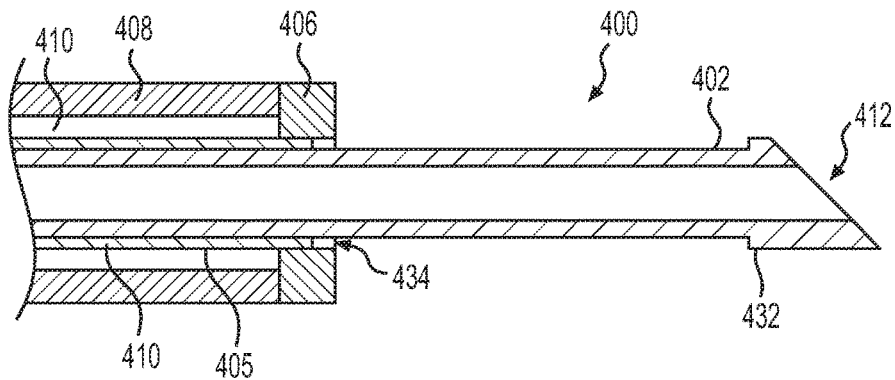
FIGS. 4A and 4B illustrate side cross-sectional views of a distal portion of an exemplary instrument, according to aspects of the present disclosure.
Figure 4B:
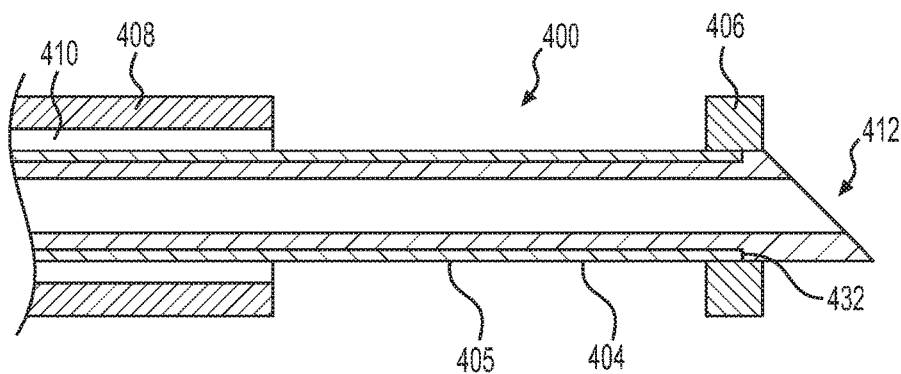

FIGS. 4A and 4B illustrate another exemplary instrument 400, which may include a sheath 408, an inner member 402, and an outer member 404 (with a shaft 405 and a protrusion 406) similar to other instruments described herein. Inner member 402 may include a protrusion 432 (e.g., an enlarged distal end). Outer member 404 may include a distal cavity, cut-out, or recess 434. Protrusion 432 may be configured to be at least partially received in recess 434 when inner member 402 is moved proximally relative to outer member 404. A proximal-facing surface of protrusion 432 may engage a distal-facing surface of outer member 404 to prevent inner member 402 from being fully retracted into outer member 404, thereby limiting retraction of inner member 402, and/or to prevent outer member 404 from being extended past inner member 402.

Figure 5:
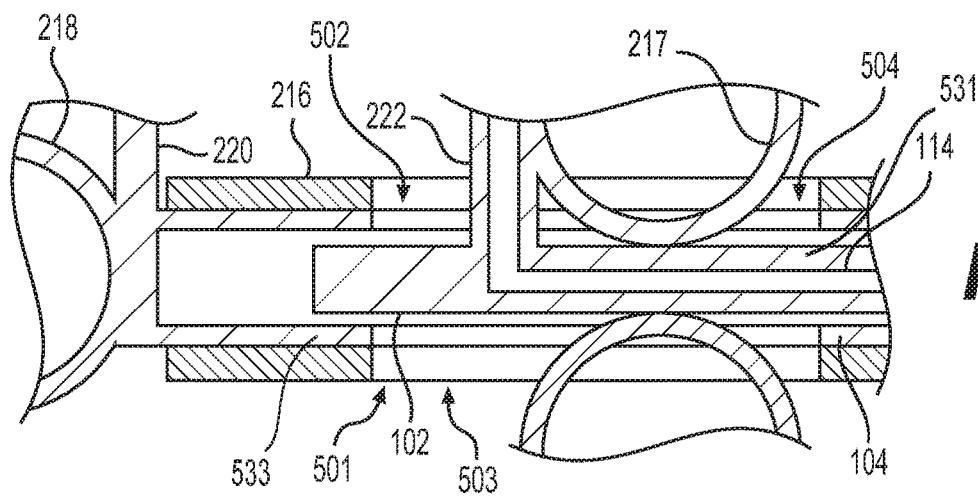
FIG. 5 illustrates a side cross-sectional view of the proximal portion of the exemplary instrument of FIGS. 1A and 1B, according to aspects of the present disclosure.

FIG. 5 shows a side cross-sectional view of handle assembly 200. In this example, the proximal portion of outer member 104, which extends proximally to outer member actuator 218, slidably receives the proximal portion of inner member 102, which extends proximally to inner member actuator 217. The proximal portions of inner and outer members 102 and 104 are slidably received by handle body 216. In some examples, the proximal portion of outer member 104 may include one or more slots 501 and 502 through which portions of inner member actuator 217 may extend. Those portions of inner member actuator 217 may slide longitudinally along slots 501 and 502. Similar slots 503 and 504 may be provided in handle body 216. Slots 501 and 502 may be aligned with slots 503 and 504. Proximal and distal ends of slots 501, 502, 503, and/or 504 may act as stops for limiting movement of one or more of inner member 102, outer member 104, and handle body 216 relative to another of inner member 102, outer member 104, and handle body 216.

Figure 6A:
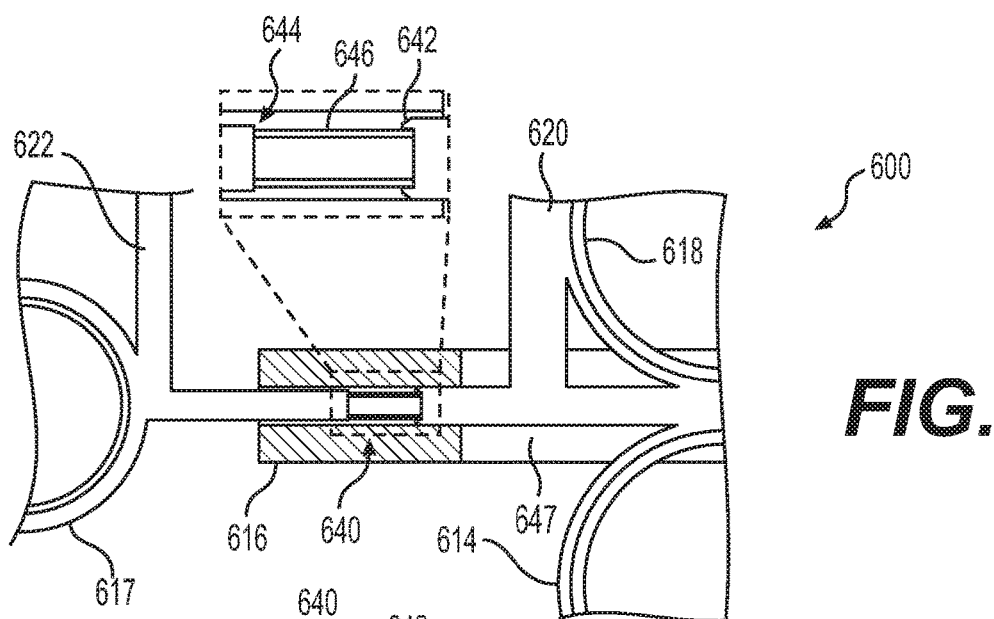
FIGS. 6A and 6B illustrate side cross-sectional views of a proximal portion of an exemplary instrument in various states, according to aspects of the present disclosure.
Figure 6B:
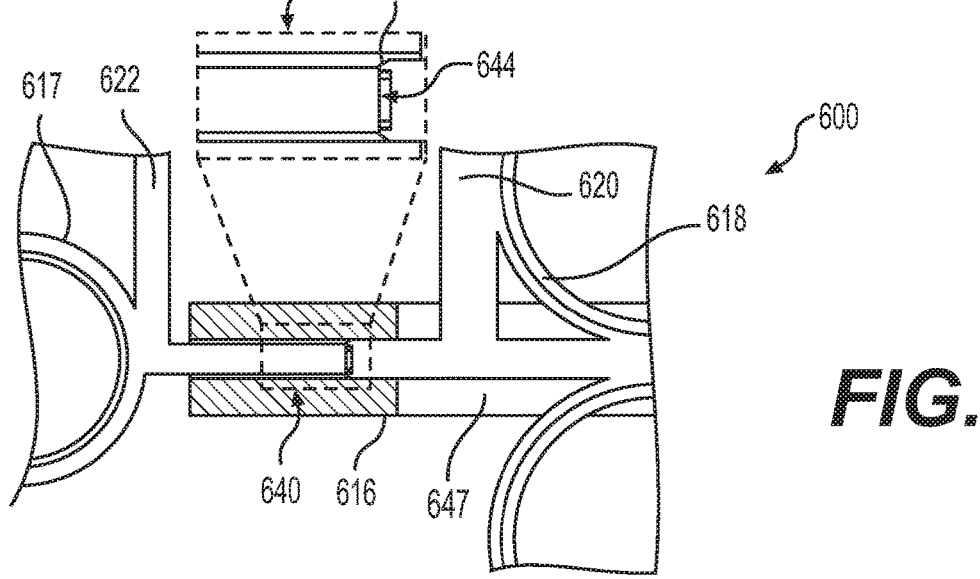

FIGS. 6A and 6B show an exemplary handle assembly 600 in which positions of an inner member actuator 617 and an outer member actuator 618 have been switched, such that outer member actuator 618 is distal to inner member actuator 617. Handle assembly 600 may include a stop assembly. More particularly, within handle body 616, a distally-facing surface 644 of inner member actuator 617 may oppose a proximally-facing surface 642 of outer member actuator 618. A portion 646 of inner member actuator 617 may slide proximally and distally, into and out of, a portion 647 of outer member actuator 618. When surfaces 644 and 642 abut, further longitudinal movement of portion 646 into portion 647 may be prevented. The abutment of surfaces 642 and 644 may limit movement of one of inner member actuator 617 and outer member actuator 618 relative to the other of inner member actuator 617 and outer member actuator 618. In handle assembly 600, inner member and outer member actuators 617 and 618 may slide longitudinally within handle body 616. Additionally or alternatively, one or more of inner member and outer member actuators 617 and 618 may rotate relative their central longitudinal axes, to rotate one or more of the inner and outer members. Either of handle assemblies 200 and 600 may be used with each of the instrument in the present disclosure.

FIGS. 7A-7E illustrate a distal portion of another exemplary instrument 700, which may include a sheath 708, an inner member 702 (with a lumen 714), and an outer member 704 (with a shaft 705 and a protrusion 706), similar to other instruments described herein. Inner member 702 may include a protrusion 752 projecting radially-outwardly therefrom at its distal end. Protrusion 752 may be positioned at a proximalmost portion of a distalmost edge of inner member 702. Protrusion 752 may be configured (e.g., sized and/or shaped) for insertion into an opening 750 at a distal-facing surface of outer member 704. Opening 750 may be connected to a slot, recess, or cavity (not shown) within outer member 704. The cavity may, for example, follow a helical path starting at opening 750 and extending proximally therefrom. Alternatively, the path may be L-shaped, with a first portion extending proximally from opening 750, which may lead to another portion extending transverse to the first portion.

Figure 7A:
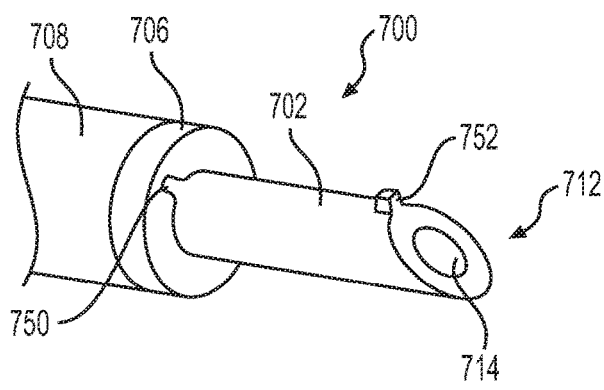
FIGS. 7A-7E illustrates perspective views of a distal portion of an exemplary instrument in various states, according to aspects of the present disclosure.
Figure 7B:
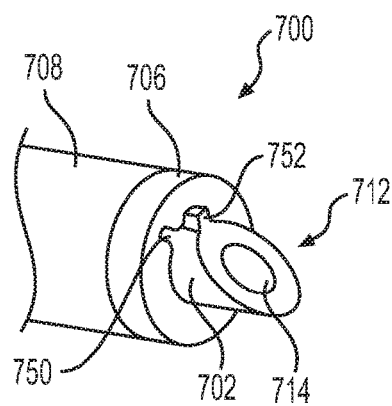
Figure 7C:
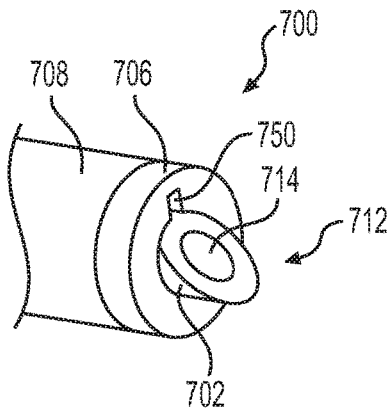
Figure 7D:
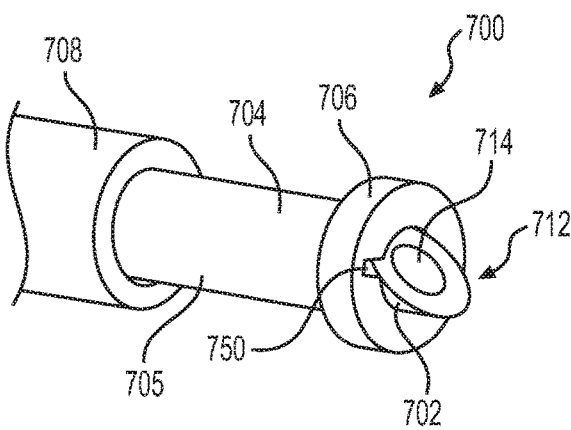
Figure 7E:
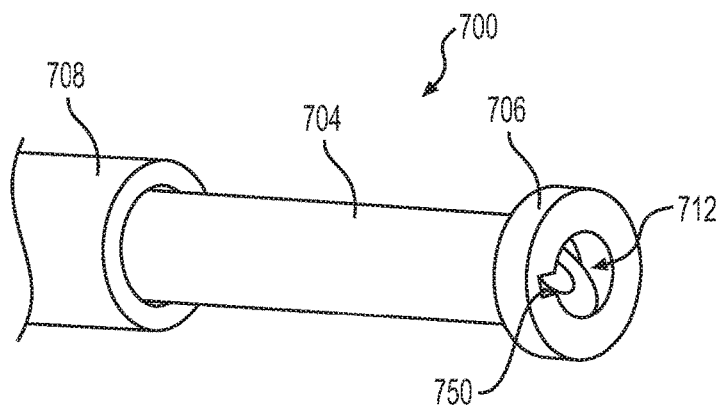

In use, inner member 702 may be rotated by the user (from either the position shown in FIG. 7A or the one shown in FIG. 7B) to align protrusion 752 with opening 750. Inner member 702 and/or outer member 704 may be moved to insert protrusion 752 into opening 750 (FIG. 7C). Once protrusion 752 is positioned within the cavity, the user may move protrusion 752 laterally such that protrusion may be offset (circumferentially) from opening 750 (FIG. 7D). Continued rotation of inner member 702, proximal sliding of inner member 702 relative to outer member 704, and/or distal sliding of outer member 704 relative to inner member 702, may result in the distal end of inner member 702 being housed entirely within outer member 704 (FIG. 7E). In the state shown in FIG. 7D and/or FIG. 7E, inner member 702 and outer member 704 may be coupled to move in the proximal and distal directions in tandem. The steps described above may be reversed to uncouple inner and outer members 702 and 704, allowing them to once again be moved independent of each other. The user may couple and uncouple the inner and outer members 702 and 704 multiple times during a single procedure, if desired, using the steps outlined above.

Figure 8A:
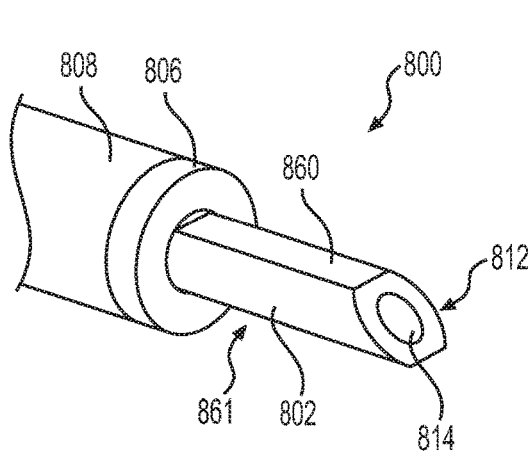
FIGS. 8A and 8B illustrate perspective views of a distal portion of an exemplary instrument in various states, according to aspects of the present disclosure.
Figure 8B:
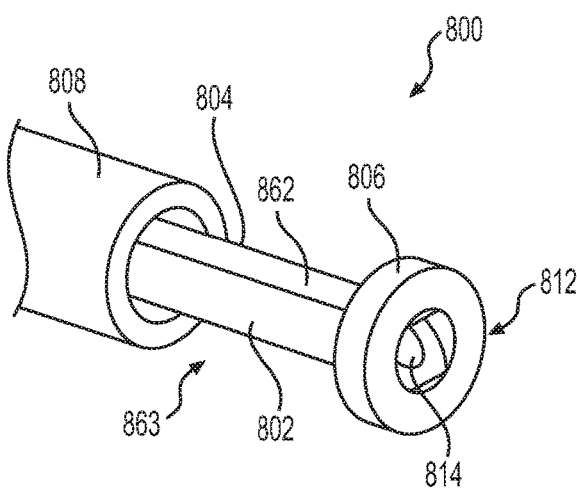

FIGS. 8A and 8B illustrate another exemplary embodiment of a medical instrument 800, which may include a sheath 808, an inner member 802 (with a lumen 814), and an outer member 804 (with a shaft 862, 863 and a protrusion 806), similar to other instruments described herein. Inner member 802 may include one or more planar surfaces 860 and 861. For example, inner member 802 may include a pair of planar surfaces 860 and 861 on opposite sides of inner member 802, that may form part of the outer surface of inner member 802. Outer member 804 may include two shaft portions 862 and 863. Shafts 862 and 863 may be coupled at their distal ends to protrusion 806. Shafts 862 and 863 may be separated by a gap configured to receive inner member 802. Shafts 862 and 863 may slide along and against planar surfaces 860 and 861. Opposite sides of inner member 802 that are in the gap may be exposed when inner member 802 is within the gap. Shafts 862 and 863 may be cylindrical segments. It is contemplated that, in combination, shafts 862 and 863, and inner member 802, may form a cylinder. One of, or both of, shafts 862 and 863 may have a D-shaped cross-section. This configuration of planar surfaces 860 and 861 and shafts 862 and 863 may help limit or prevent relative rotation between inner and outer members 802 and 804. Accordingly, rotating one of inner and outer members 802 and 804 may result in rotation of the other of inner and outer members 802 and 804. It also is contemplated that planar surface 861 and shaft 863 may be omitted, such that inner member 802 may only have one lateral planar surface, and one shaft to move slidably along that surface.

Figure 9A:
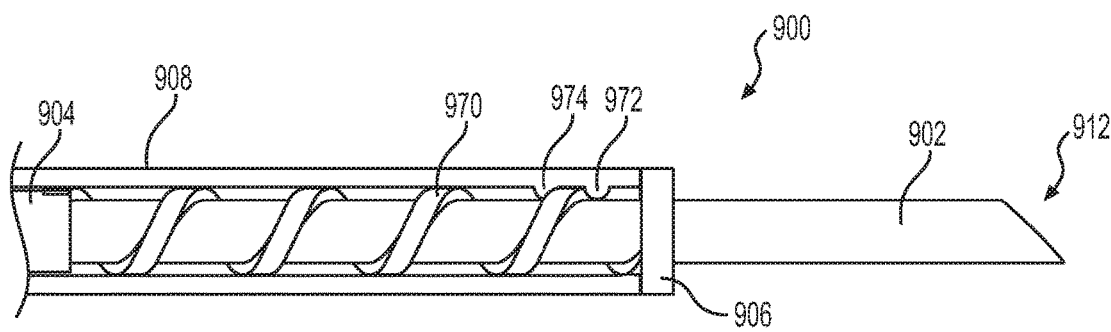
FIGS. 9A and 9B illustrate perspective views of a distal portion of an exemplary instrument in various states, according to aspects of the present disclosure.
Figure 9B:
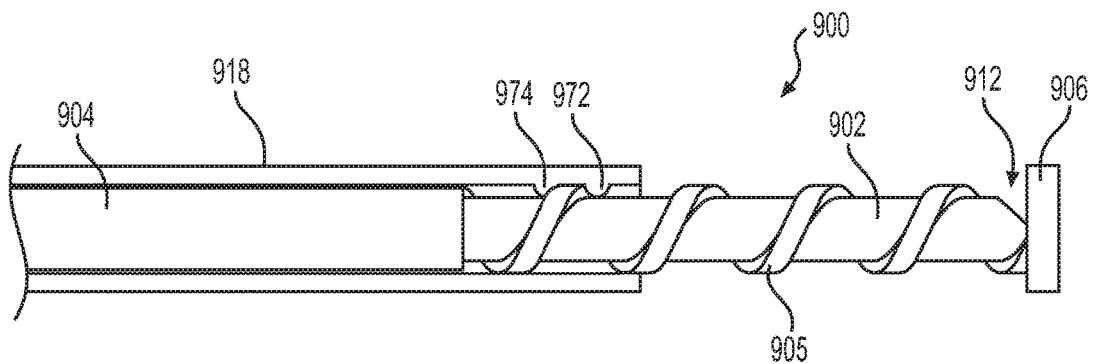

FIGS. 9A and 9B illustrate another exemplary embodiment of a medical instrument 900, which may include a sheath 908, an inner member 902 (with a lumen (not shown)), and an outer member 904 (with a shaft 905 and a protrusion 906), similar to other instruments described herein. Shaft 905 may be helical. Protrusions 972 and 974 may be positioned on a radially-inner surface of sheath 908 to engage shaft 905. The user may move outer member 904 longitudinally, in the proximal or distal directions, by rotating outer member 902 about its central longitudinal axis, which may cause a camming action between the helical turns of shaft 905 and protrusions 972 and 974 that converts the rotation into longitudinal travel. In some examples, a force exerted on outer member 905 in the proximal-distal direction may not cause longitudinal movement of outer member 905, due to the obstruction posed by contact between protrusions 972 and 974 and the helical turns of outer member 905. Alternatively, protrusions 972 and/or 974 may be omitted to facilitate longitudinal movement of outer member 905 relative to sheath 908 via sliding or translation.

Figure 10A:
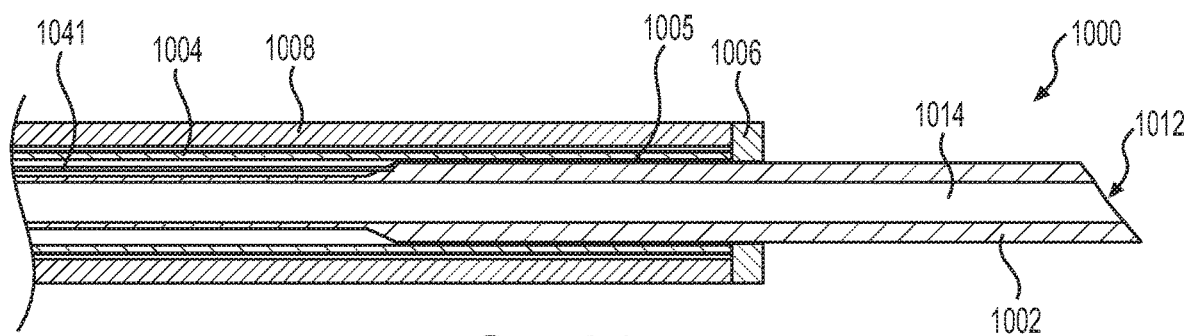
FIGS. 10A and 10B illustrate side cross-sectional views of a distal portion of an exemplary instrument in various states, according to aspects of the present disclosure.
Figure 10B:
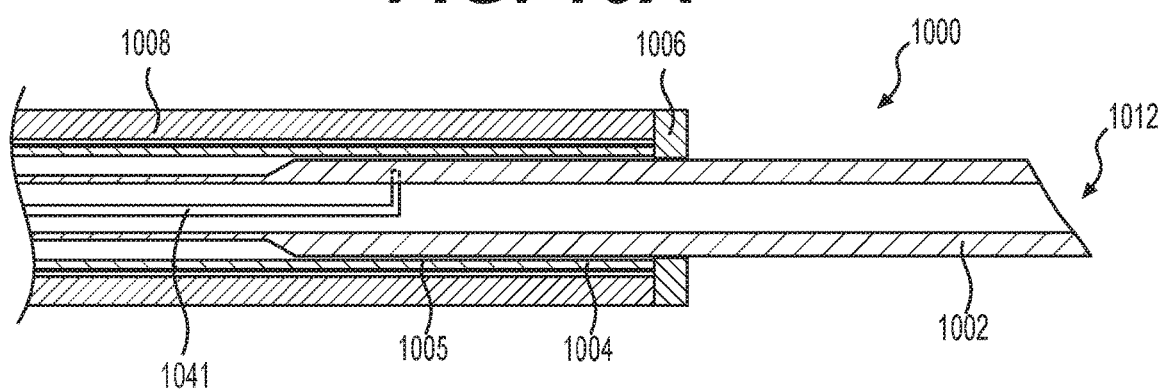

FIGS. 10A and 10B illustrate two different examples of an instrument 1000, which may include a sheath 1008, an inner member 1002 (with a lumen 1014), and an outer member 1004 (with a shaft 1005 and a protrusion 1006), similar to other instruments described herein. As shown in FIG. 10A, an electrical element 1041, which may extend from, for example, electrical connector 220 (FIG. 5) or 620 (FIGS. 6A and 6B), to a distal portion of outer member 1004 and/or inner member 1002, via a space between a radially-outer surface of inner member 1002 and a radially-inner surface of outer member 1004. Or, as shown in FIG. 10B, electrical element 1041 may extend through lumen 1014. In other examples, an electrical element may be integrated into the wall structure of outer member 1004 and/or inner member 1002. In some examples, outer member 1004 and/or inner member 1002 may be an electrical element, through construction of the member(s) using conductive material(s). In this example, and in any of the other examples of inner and outer members described herein, one of the inner and outer members may be conductive (to act as an electrode), while the other is non-conductive (to act as an insulator); or both of the members may be conductive such that both may act as electrodes.

Figure 11A:
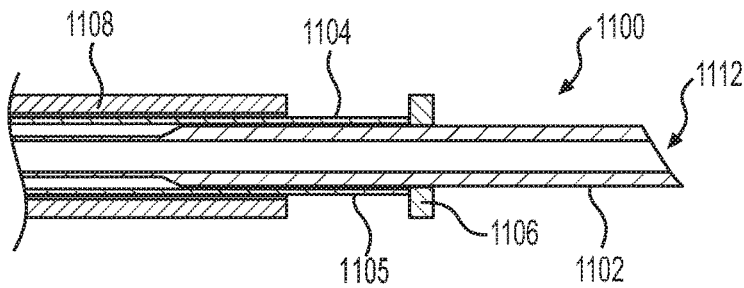
FIGS. 11A-11C illustrate side cross-sectional views of a distal portion of an exemplary instrument in various states, according to aspects of the present disclosure.
Figure 11B:
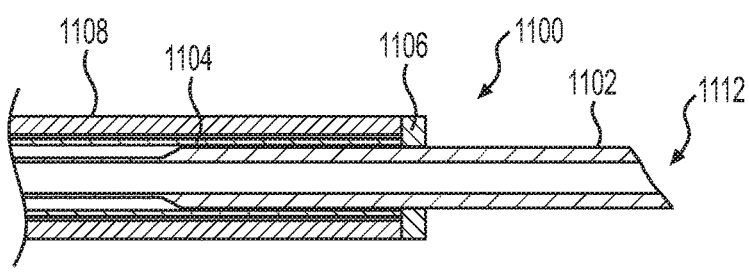
Figure 11C:
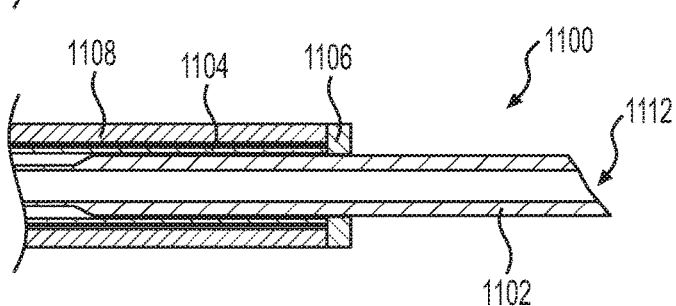

FIGS. 11A-11C illustrate yet another exemplary instrument 1100, which may include a sheath 1108, an inner member 1102, and an outer member 1104 (with a shaft 1105 and a protrusion 1106), similar to other instruments described herein. Sheath 1108 and/or outer member 1104 may be moved from the state in FIG. 11A to that of FIG. 11B to cause sheath 1108 to engage outer member 1104, at or near the distal end of outer member 1104, in a manner that couples sheath 1108 to outer member 1104. For example, sheath 1108 may engage a distal end of shaft 1105 and/or a proximal-facing surface of protrusion 1106. Once coupled, sheath 1108 and outer member 1104 may move in tandem, such that sheath 1108 may be used to move outer member 1104 proximally to expose inner member 1102 (see FIGS. 11B and 11C), or hold outer member 1104 while inner member 1102 is extended therefrom. The coupling of sheath 1108 to outer member 1104 may be facilitated using any suitable locking or latching mechanism, including frictional fit, snap-fit, detent, and/or interference.

In use of any of the aforementioned instruments (100, 300, 400, 600, 700, 800, 900, 1000, 1100), the user may locate a treatment site (such as a tumor, lesion, or other diseased tissue) present in a subject's body using an endoscope or other tool (FIG. 3A). The endoscope may include an image sensor at its distal end to provide direct visualization of the treatment site. Any of the aforementioned instruments may be inserted through the endoscope until the distal portion of the instrument is at the treatment site. The protrusion of the outer member of the instrument may be energized by electrical energy from the energy source, and the user may press the protrusion against tissue to mark the tissue. The outer member may be extended (e.g., protruding distally from the outer sheath) or retracted (e.g., housed within the outer sheath) during marking. Each of the inner member, the outer member, and the outer sheath may be moved independently of the others by appropriate manipulation of the inner member actuator, the outer member actuator, and the handle body. It should be understood, however, that the user may move one or more of the inner member, the outer member, and the outer sheath together, if desired, by coordinating manipulation of the inner member actuator, the outer member actuator, and the handle body, or by coupling one component to another, so they move in tandem, using any of the aforementioned mechanisms.

The user may then move the outer member proximally, the sheath proximally, and/or move the inner member distally to project the inner member distally from the outer member. The user may pierce the tissue using the inner member, either with or without the assistance of electrical energy, and may insert the inner member into the tissue to a desired insertion depth. The user may inject fluid from the fluid source into the tissue, which may separate overlying layers of the tissue from underlying layers, thereby providing a separation between the layers that may ensure that the underlying layers are not accidentally damaged during the next steps.

The user may then move the outer member distally, the sheath proximally, and/or the inner member proximally, to have the outer member protrude distally from the outer sheath while also housing the distal end of the inner member in the outer member. The user may then energize the outer member using electrical energy from the energy source, and use the outer member to cut the raised overlying layers using the shaft and/or the protrusion of the outer member. The user may repeat the injecting and cutting steps as many times as necessary to complete the procedure. For example, until the overlying layers are sufficiently dissected, or completely resected. In one example involving the gastrointestinal tract, the overlying layers may include one or more of the mucosa and the submucosa, while the underlying layer may include the muscularis. Using the instruments described herein, such procedures may be carried out without wasting time switching between tools to perform injection and cutting.

It should be understood that one or more of the aspects of any of the instruments described herein may be used in combination with any of the other instruments. It also should also be understood that one or more aspects of any of the instruments described herein may be used for cutting, dissecting, treating, insufflating, injecting with liquid, or ablating tissue in any part of the human body. For example any of the medical instruments described herein may be used in medical procedures such as for Endoscopic Submucosal Dissection (ESD), cancer treatment, and/or other procedures where removal, dissection, insufflation, perforation, and/or ablation of the type of tissue is needed.

Moreover, while specific exemplary embodiments may have been illustrated and described collectively herein, it should be appreciated that any subsequent arrangement designed to achieve the same or similar purpose may be substituted for the specific embodiments described and shown herein. This disclosure is intended to cover any and all subsequent adaptations or variations of various embodiments. Combinations of the above embodiments, and other embodiments not specifically described herein, will be apparent to those of skill in the art upon reviewing the description.

Other exemplary embodiments of the present disclosure will be apparent to those skilled in the art from consideration of the specification and practice of the exemplary embodiments disclosed herein. It is intended that the specification and examples be considered as exemplary only, and departures in form and detail may be made without departing from the scope and spirit of the present disclosure as defined by the following claims.

We claim:

1. An instrument, comprising:
a sheath having a distal end;
a fluid cannula at the distal end of the sheath; and
a cutting electrode at the distal end of the sheath, wherein at least one of: (i) an exterior surface of the fluid cannula, or (ii) a cutting electrode surface that faces the exterior surface, is longitudinally slidable along the other of the exterior surface and the cutting electrode surface during movement of at least one of the cutting electrode or the fluid cannula relative to the other of the cutting electrode and the fluid cannula, wherein the fluid cannula includes an enlarged distal portion at a distal end of a tubular portion of the fluid cannula, wherein the enlarged distal portion is wider than the tubular portion, and wherein a distal end of the enlarged distal portion includes a sharpened tip, wherein the fluid cannula and the cutting electrode are movable from a first configuration, in which the fluid cannula and the cutting electrode are independently movable, to a second configuration, in which the fluid cannula and the cutting electrode are coupled so as to move in unison, wherein the cutting electrode includes a protrusion on a distal end of the cutting electrode, wherein an entirety of the protrusion is non-conductive, and wherein at least one of the cutting electrode or the fluid cannula is movable relative to the other of the cutting electrode and the fluid cannula between respective extended configurations and respective retracted configurations relative to the distal end of the sheath, wherein a distal portion of the protrusion includes a recess, and wherein (a) when the fluid cannula and the cutting electrode are in the retracted configurations, (1) a proximal face of the protrusion abuts a distal face of the sheath, (2) the recess receives at least a portion of the enlarged distal portion such that a proximal face of the enlarged distal portion abuts an annular distal face of the recess of the protrusion, and (3) the sharpened tip of the distal end of the fluid cannula extends distally of a distal end of the protrusion of the cutting electrode; and and (b) when the fluid cannula and the cutting electrode are in the extended configurations (1) the recess receives at least a portion of the enlarged distal portion such that a proximal face of the enlarged distal portion abuts an annular distal face of the recess of the protrusion, and (2) the sharpened tip of the distal end of the fluid cannula extends distally of a distal end of the protrusion of the cutting electrode.

2. The instrument of claim 1, wherein the cutting electrode surface is an interior surface of the cutting electrode.

3. The instrument of claim 1, wherein the cutting electrode surface is a radially-inner surface of the cutting electrode.

4. The instrument of claim 1, wherein the cutting electrode surface is one of a plurality of spaced-apart cutting electrode surfaces that face the exterior surface of the fluid cannula.

5. The instrument of claim 1, wherein the cutting electrode surface is an interior surface of the tubular portion.

6. The instrument of claim 1, wherein the sharpened tip of the fluid cannula terminates at a distal point configured to pierce tissue.

7. The instrument of claim 1, wherein at least one of the cutting electrode or the fluid cannula is movable relative to the other of the cutting electrode or the fluid cannula to position a distal end of the fluid cannula distal to a distal end of the cutting electrode.

8. The instrument of claim 1, wherein at least a portion of the fluid cannula is electrically conductive, wherein the sheath includes a lumen that extends along a central longitudinal axis of the sheath to deliver fluid, wherein the fluid cannula includes a passage to deliver the fluid that is longitudinally aligned with the lumen of the sheath, and wherein a flow of the fluid through the lumen of the sheath and the passage of the fluid cannula is longitudinally aligned with the central longitudinal axis of the sheath.

9. An instrument, comprising:
a sheath having a distal end;
a first electrode at the distal end of the sheath, wherein the first electrode includes:
  a passage extending therethrough for directing a fluid through the first electrode, and
  a distal opening from which the fluid is emitted from the first electrode;
a second electrode at the distal end of the sheath, wherein:
  an exterior surface of the second electrode is configured to cut tissue,
  one of the first electrode and the second electrode is movable relative to the other of the first electrode and the second electrode, and
at least a portion of the second electrode slidably receives at least a portion of the first electrode, and
a handle assembly at a proximal end of the sheath, wherein the handle assembly includes a first actuator and a second actuator, wherein movement of the first actuator moves the first electrode relative to at least one of the distal end of the sheath or the second electrode, wherein movement of the second actuator moves the second electrode relative to at least one of the distal end of the sheath or the first electrode, and wherein the first actuator includes a fluid connector configured to be coupled to a fluid source to deliver fluid from the fluid source through the fluid connector and through the passage of the first electrode, wherein the second electrode includes a protrusion that extends radially outward at the distal end of the second electrode, wherein the first electrode includes a sharpened tip, wherein an entirety of the protrusion is non-conductive, wherein a distal portion of the protrusion includes a recess, wherein the second electrode with the protrusion forms a smaller ablation zone than the first electrode, wherein the first electrode includes an enlarged distal portion, wherein the enlarged distal portion of the first electrode includes a non-tapered proximal portion and a tapered distal portion, and wherein the first and second electrodes are movable relative to the sheath between respective extended configurations relative to a distal end of the sheath and respective retracted configurations relative to the distal end of the sheath, and wherein, (a) when the first electrode and the second electrode are in the retracted configurations, (1) a proximal face of the protrusion abuts a distal face of the sheath, (2) a radially outer surface of the enlarged distal portion contacts a radially inner surface of the protrusion, and (3) the non-tapered proximal portion of the enlarged distal portion of the first electrode overlaps with the protrusion of the second electrode, and the tapered distal portion of the enlarged distal portion of the first electrode extends distally of a distal end of the non-conductive protrusion of the second electrode; and (b) when the first electrode and the second electrode are in the extended configurations, (1) a radially outer surface of the enlarged distal portion contacts a radially inner surface of the protrusion, and (2) the non-tapered proximal portion of the enlarged distal portion of the first electrode overlaps with the protrusion of the second electrode, and the tapered distal portion of the enlarged distal portion of the first electrode extends distally of a distal end of the non-conductive protrusion of the second electrode.

10. The instrument of claim 9, wherein the handle assembly further includes a handle body, and wherein the first and second actuators are each slidably coupled to the handle body, and the sheath is fixed relative to the handle body,
wherein the sheath includes a lumen that extends along a central longitudinal axis of the sheath to deliver fluid,
wherein the first electrode includes a passage to deliver the fluid that is longitudinally aligned with the lumen of the sheath, and
wherein a flow of the fluid through the lumen of the sheath and the passage of the first electrode is longitudinally aligned with the central longitudinal axis of the sheath.

11. The instrument of claim 10, wherein at least one of the first or second actuators is rotatably coupled to the handle body, such that rotation of the at least one of the first or second actuators relative to the handle body rotates at least one of the first or second electrodes about at least one of their respective central longitudinal axes.

12. The instrument of claim 9, wherein central longitudinal axes of the first and second electrodes are coaxial, and
wherein the first electrode and the second electrode are movable from a first configuration, in which the first electrode and the second electrode are independently movable, to a second configuration, in which distal portions of the first electrode and the second electrode are coupled via a locking or latching mechanism so as to move in unison.

13. A method for treating tissue in a target area of a subject, the method comprising:
positioning a distal end of an instrument at the target area, wherein the instrument includes a sheath, and wherein the sheath includes a fluid lumen;
moving at least one of a first electrode or a second electrode, at the distal end of the instrument, relative to the other of the first and second electrodes, to position a distal end of the first electrode distal to a distalmost end of the second electrode, wherein the first electrode includes an internal passage fluidly connected to a fluid source via a fluid connector on a handle assembly, wherein the first electrode and the second electrode are coaxial, with the second electrode radially surrounding the first electrode, and wherein the second electrode includes a protrusion that extends radially outward at a distal end of the second electrode, wherein an entirety of the protrusion is non-conductive, wherein the first electrode includes an enlarged portion on a distal end, wherein the enlarged portion on the distal end of the first electrode includes a non-tapered proximal portion and a tapered distal portion, and wherein a distal portion of the protrusion of the second electrode includes a recess configured to receive at least a portion of the enlarged portion such that a proximal face of the enlarged portion abuts an annular distal face of the recess of the protrusion when the protrusion of second electrode overlaps with the enlarged portion of the first electrode,
wherein the fluid lumen of the sheath extends along a central longitudinal axis of the sheath to deliver fluid,
wherein the first electrode includes a passage to deliver the fluid that is longitudinally aligned with the lumen of the sheath, and
wherein a flow of the fluid through the lumen of the sheath and the passage of the first electrode is longitudinally aligned with the central longitudinal axis of the sheath;
puncturing the tissue with the distal end of the first electrode, wherein the distal end of the first electrode includes a sharpened tip;
injecting fluid into the tissue through the first electrode to raise the tissue;
moving at least one of the first or second electrodes relative to the other of the first and second electrodes, (1) to cover the non-tapered proximal portion of the enlarged portion of the first electrode with the distal end of the second electrode such that a proximal face of the enlarged portion of the first electrode abuts an annular distal face of the recess of the protrusion, (2) a proximal face of the protrusion abuts a distal face of a sheath, and (3) the tapered distal portion of the enlarged portion of the first electrode extends distally of a distal end of the non-conductive protrusion of the second electrode; and
energizing the second electrode with electrical energy to cut the raised tissue.

14. The method of claim 13, wherein the first electrode and the second electrode are movable from a first configuration, in which the first electrode and the second electrode are independently movable, to a second configuration, in which distal portions of the first electrode and the second electrode are coupled via a locking or latching mechanism so as to move in unison.

15. The method of claim 14, wherein moving at least one of the first or second electrodes relative to the other of the first and second electrodes, to cover at least a portion of the first electrode with the distal end of the second electrode, causes the first electrode to form a smaller ablation zone than the one of the first electrode or the second electrode that does not include the protrusion,
wherein the first and second electrodes are movable relative to the sheath between respective extended configurations relative to a distal end of the sheath and respective retracted configurations relative to the distal end of the sheath.

16. The instrument of claim 9, further comprising an electrical element, wherein the electrical element extends from an electrical connector on the handle to one or more of the first electrode or the second electrode.

17. The instrument of claim 12, further comprising an electrical element, wherein the electrical element extends from an electrical connector on the handle assembly to one or more of the first electrode or the second electrode.

18. The method of claim 15, wherein energizing the first and second electrodes includes delivering energy to the first and second electrodes via an electrical element that extends from an electrical connector on the handle assembly to the first and second electrodes.

19. The method of claim 13, wherein a radially outer surface of the enlarged portion contacts a radially inner surface of the protrusion.

20. The instrument of claim 1, wherein a radially outer surface of the enlarged distal portion contacts a radially inner surface of the protrusion.

* * * * *